(12) United States Patent
Castaldi et al.

(10) Patent No.: US 8,203,002 B2
(45) Date of Patent: Jun. 19, 2012

(54) INTERMEDIATES FOR THE PREPARATION OF PRAMIPEXOLE

(75) Inventors: Graziano Castaldi, Briona (IT); Alberto Bologna, Crema (IT); Pietro Allegrini, San Donato Milanese (IT); Gabriele Razzetti, Sesto San Giovanni (IT); Vittorio Lucchini, San Donato Milanese (IT)

(73) Assignee: Dipharma S.p.A., Mereto di Tomba (IT)

( * ) Notice: Subject to any disclaimer, the term of this patent is extended or adjusted under 35 U.S.C. 154(b) by 250 days.

(21) Appl. No.: 12/776,588

(22) Filed: May 10, 2010

(65) Prior Publication Data

US 2010/0222595 A1    Sep. 2, 2010

Related U.S. Application Data

(62) Division of application No. 10/593,269, filed as application No. PCT/EP2005/002641 on Mar. 11, 2005, now Pat. No. 7,741,490.

(30) Foreign Application Priority Data

Mar. 19, 2004  (IT) ............................... MI2004A0531
Jan. 28, 2005  (IT) ............................... MI2005A0126

(51) Int. Cl.
$C07D\ 277/82$     (2006.01)
(52) U.S. Cl. ...................................................... 548/164
(58) Field of Classification Search .................. 548/164
See application file for complete search history.

(56) References Cited

U.S. PATENT DOCUMENTS 4,988,699 A     1/1991   Caprathe et al.

FOREIGN PATENT DOCUMENTS

WO     2004/083218 A     9/2004

OTHER PUBLICATIONS

Schneider et al., "Dopamine Autoreceptor Agonists: Resolution and Pharmacological Activity of 2, 6-Diaminotetrahydrobenzothiazole . . . ", Journal of Medicinal Chemistry, vol. 30, No. 3, Mar. 1987, pp. 494-498.

*Primary Examiner* — Laura L. Stockton
(74) *Attorney, Agent, or Firm* — Rothwell, Figg, Ernst & Manbeck, P.C.

(57) ABSTRACT

Intermediates useful for the preparation of pramipexole and the use thereof in such synthesis.

5 Claims, No Drawings

INTERMEDIATES FOR THE PREPARATION OF PRAMIPEXOLE

This application is a divisional of 10/593,269 filed Sep. 18, 2006 which is a 35 U.S.C. 371 National Phase Entry Application from PCT/EP2005/002641, filed Mar. 11, 2005, which claims the benefit of Italian Patent Applications No. MI2004A000531 filed on Mar. 19, 2004 and MI2005A000126 filed Jan. 28, 2005, the disclosures of which are incorporated herein in their entirety by reference.

FIELD OF THE INVENTION

The present invention relates to novel intermediates useful in the preparation of pramipexole or (S)-2-amino-6-n-propylamino-4,5,6,7-tetrahydrobenzothiazole and a novel method for its preparation.

TECHNOLOGICAL BACKGROUND

Pramipexole, of formula (A)

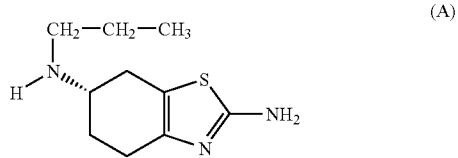

is a dopaminergic agonist, known from U.S. Pat. No. 4,843,086, used in the treatment of Parkinson's disease in the form of dihydrochloride monohydrate.

US 2002/0103240 discloses inter alia a method for the resolution or the enrichment of (R,S)-2-amino-6-propylamino-4,5,6,7-tetrahydrobenzothiazole in the single (R) or (S) enantiomers, in particular in the (S) enantiomer. The same application illustrates in detail the synthetic routes known for the preparation of pramipexole, in particular those described in U.S. Pat. No. 4,886,812, EP 186087, EP 207696 and J. Med. Chem. 30. 494 (1987). From what reported it is evident that the synthetic pathways up to now available make use of synthetic steps that do not fulfill the requirements for the production of pramipexole on the industrial scale. Therefore there is the need for an improved process, which is simpler, easier to carry out and meets the requirements for the industrial production of pramipexole.

SUMMARY OF THE INVENTION

It has now been found a process for the preparation of pramipexole, which employs novel intermediates and fulfils the requirements for the production in industrial amounts.

DETAILED DISCLOSURE OF THE INVENTION

The present invention relates to a compound of formula (I), both as a mixture of (R,S) enantiomers, and as the single (R) or (S) enantiomers, or a salt thereof,

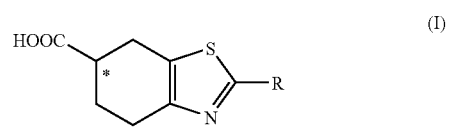

wherein R is a protected amino group; and the asterisk * indicates the stereogenic carbon atom.

A salt of a compound of formula (I) can be a salt with bases or acids, organic or inorganic. Preferred examples of salts with bases are those with inorganic bases, such as sodium, lithium or potassium salts, or salts with primary, secondary or tertiary amines, such as N-methyl-, N,N-dimethyl- and triethyl-ammonium salts, benzylammonium, α-methylbenzylamine, N-methyl-D-glucamine, cinchonidine or cinchonine salts. Preferred examples of salts with acids are those with hydrochloric, sulfuric, acetic, oxalic or methanesulfonic acids, preferably with an optically active acid, such as tartaric or camphorsulfonic acid.

Preferably a compound of formula (I), or a salt thereof, is in the form of the single (R) or (S) enantiomer, in particular as the single (S) enantiomer, typically with at least approx. 96%, more preferably at least approx. 99%, enantiomeric purity.

Preferred examples of the compounds of formula (I) are:
  (S)-2-acetylamino-4,5,6,7-tetrahydro-benzothiazole-6-carboxylic acid;
  (S)-2-propionylamino-4,5,6,7-tetrahydro-benzothiazole-6-carboxylic acid;
  (R)-2-acetylamino-4,5,6,7-tetrahydro-benzothiazole-6-carboxylic acid; and
  (R)-2-propionylamino-4,5,6,7-tetrahydro-benzothiazole-6-carboxylic acid.

A compound of formula (I), as defined above, either as a mixture of (R,S) enantiomers or as single (R) or (S) enantiomer, can be obtained with a process comprising the hydrolysis of an ester of formula (II) or a salt thereof, either as a mixture of (R,S) enantiomers or as single (R) or (S) enantiomer

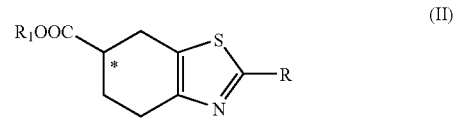

wherein $R_1$ is straight or branched $C_1$-$C_6$ alkyl, optionally substituted with phenyl; and the asterisk * and R have the meanings defined above;

and, if desired, the resolution of the mixture of (R,S) enantiomers of the compound of formula (I) to yield the single (R) or (S) enantiomer.

$R_1$ is preferably a $C_1$-$C_4$ alkyl group, such as methyl, ethyl, n-propyl, isopropyl, n-butyl, isobutyl or tert-butyl, in particular ethyl or propyl; or benzyl or phenylethyl.

A salt of a compound of formula (II) is for example a salt with a mineral acid, preferably an hydrohalic acid, in particular hydrochloric or hydrobromic acid, or an organic acid, such as acetic, oxalic or methanesulfonic acid, preferably an optically active acid, such as tartaric or camphorsulfonic acid.

According to the present invention, a protected amino group R can be, for example, a protected amino group in the form of an acylamino, carbamoyl, arylmethylamino, phthalimido or silylamino group.

In an acylamino group, acyl is for example formyl or $C_1$-$C_6$—CO— alkyl, preferably acetyl, propionyl or pivaloyl, optionally substituted with 1 to 3 halogen atoms, such as chlorine, fluorine, bromine or iodine.

In a carbamoyl group, the amino group is linked, for example, to a $C_1$-$C_6$ alkoxy-carbonyl group, wherein the alkyl residue is straight or branched, optionally substituted with phenyl. The alkyl residue is preferably a $C_1$-$C_4$ alkyl group, optionally substituted with phenyl, such as methyl, ethyl, n-propyl, isopropyl, n-butyl, isobutyl, tert-butyl, benzyl or phenylethyl, in particular tert-butyl.

In an arylmethylamino group, for example a mono, di- or particularly tri-arylmethylamino group, the aryl moiety is preferably a phenyl group. Said group is for example benzyl-, diphenylmethyl- or trityl-amino; more particularly a 1-methyl-1-phenyl-ethylamino group.

A silylamino group is for example a trimethylsilylamino or tert-butyl-dimethylsilylamino group.

A protected amino group R is preferably a protected amino group such as an acylamino or arylmethylamino group, in particular acylamino, wherein acyl is formyl, acetyl, propionyl or pivaloyl, the latter three being optionally substituted with 1 to 3 halogen atoms, such as chlorine, fluorine, bromine or iodine. More preferably the R group is acetylamino, propionylamino or pivaloylamino.

The hydrolysis of a compound of formula (II) can be carried out by reaction with an alkali hydroxide, for example sodium or potassium hydroxide, in amounts from about 1 to 4 equivalents, preferably from 1.5 to 2.5 equivalents, in a polar protic solvent, for example water or $C_1$-$C_4$ alkanols, in particular methanol, ethanol, i-propanol, or mixtures thereof; at a temperature ranging from about 0° C. to the solvent reflux, preferably from about 10 to 50° C., in particular at approx. 20° C.

According to the invention, a mixture of (R,S) enantiomers can contain the two single enantiomers in any ratio to each other. The enantiomeric purity is generally expressed as "enantiomeric excess" and defined, for example, for the (S) enantiomer as (S−R)/(R+S)×100 wherein S and R are respectively the amounts of the (S) and (R) enantiomers. According to the invention, the expression single (S) or (R) enantiomer means that the enantiomeric purity is usually at least about 96%, preferably at least about 99%.

The optional resolution of the mixture of (R,S) enantiomers of a compound of formula (I) into the single (R) or (S) enantiomers can be carried out, for example, by fractional crystallization of the diastereomeric salts of a compound of formula (I) obtained by reaction with optically active, enantiomerically pure acids or bases. An example is the reaction of the compound of formula (I) with an enantiomerically pure aliphatic or aromatic amine, for example α-methylbenzylamine, N-methyl-D-glucamine, cinchonidine and cinchonine; or with an enantiomerically pure acid, for example tartaric acid or camphorsulfonic acid, in a solvent capable of promoting the formation of the salt and the subsequent precipitation of the desired diastereomer. Examples of said solvents are $C_1$-$C_4$ alkanols, such as methanol, ethanol and i-propanol; ketones, such as acetone; ethers such as tetrahydrofuran and dioxane; alkyl esters, such as ethyl acetate; amides, such as dimethylformamide and dimethylacetamide; dimethylsulfoxide; or mixtures thereof or mixtures of one or more of them with water. The temperature can range from room temperature to the solvent reflux temperature. Alternatively, the resolution can be carried out by means of preparative chromatography using a chiral, optically active stationary phase, including the "Simulating Moving Bed" (SMB) technology. A further alternative consists in the enzymatic resolution, either by selective hydrolysis of one stereoisomer of an ester of formula (II) to an acid of formula (I), or by selective esterification of one stereoisomer of an acid of formula (I) to an ester of formula (II).

The conversion of a compound of formula (I) into a salt thereof can be obtained with known methods.

An object of the invention is also a compound of formula (II), and the salts thereof, as a mixture of (R,S) enantiomers and as the single (R) or (S) enantiomers.

Preferably a compound of formula (II), or a salt thereof, is in the form of the single (R) or (S) enantiomer, in particular as the single (S) enantiomer, typically with at least approx. 96%, more preferably at least approx. 99%, enantiomeric purity.

U.S. Pat. No. 4,988,699 generally discloses compounds of formula (I) and of formula (II) as (R,S) mixtures in which the R substituent is an amino group optionally substituted with various groups, inter alia lower alkanoyl groups. On the other hand, this patent only describes compounds with unsubstituted amino groups. The following specific acids and esters, as well as the salts thereof, although generically included within the general formula of U.S. Pat. No. 4,988,699, are to be considered novel and are a further object of the invention:

2-acetylamino-4,5,6,7-tetrahydro-benzothiazole-6-carboxylic acid;
2-propionylamino-4,5,6,7-tetrahydro-benzothiazole-6-carboxylic acid;
2-acetylamino-4,5,6,7-tetrahydro-benzothiazole-6-carboxylic acid methyl ester;
2-acetylamino-4,5,6,7-tetrahydro-benzothiazole-6-carboxylic acid ethyl ester;
2-acetylamino-4,5,6,7-tetrahydro-benzothiazole-6-carboxylic acid propyl ester;
2-propionylamino-4,5,6,7-tetrahydro-benzothiazole-6-carboxylic acid methyl ester;
2-propionylamino-4,5,6,7-tetrahydro-benzothiazole-6-carboxylic acid ethyl ester; and
2-propionylamino-4,5,6,7-tetrahydro-benzothiazole-6-carboxylic acid propyl ester.

A compound of formula (II), and the salts thereof, can be obtained by converting the amino group of a compound of formula (III)

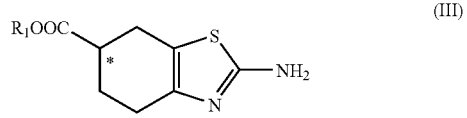

wherein $R_1$ and the asterisk * have the meanings reported above, into a protected amino group R as defined above, and optional resolution of the mixture of (R,S) enantiomers of a resulting compound of formula (II) into the single (R) or (S) enantiomers thereof, and/or salification thereof.

The conversion of the amino group of a compound of formula (II) to a protected amino group R, preferably in an acylamino, carbamoyl, arylmethylamino, phthalimido or silylamino group, as well as the salification, can be carried out according to known methods. The protection as an acylamino or carbamoyl group is preferably carried out by reaction with the corresponding anhydride, in particular acetic anhydride, or acyl-chloride or alkoxycarbonyl-chloride, in particular acetyl-chloride or methoxy- or ethoxy-carbonyl-chloride, in a solvent selected for example from acetone, acetonitrile, tetrahydrofuran, dioxane, dichloromethane or toluene; in the presence of a basic agent, preferably triethylamine, diisopropylamine or pyridine. The reaction is carried out from about −15° C. to the solvent reflux, preferably between about 0° C.

and 50° C., in particular at room temperature. The optional resolution of a mixture of (R,S) enantiomers of a compound of formula (II) into the single (R) or (S) enantiomers can be obtained, for example, by reaction with an organic acid, according to the procedures reported above for the resolution of a mixture of (R,S) enantiomers of a compound of formula (I). A compound of formula (III) can be prepared by reaction of a compound of formula (IV),

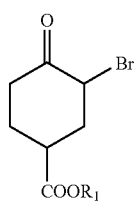

(IV)

wherein $R_1$ is as defined above, with thiourea. The cyclization reaction is carried out in an organic solvent, for example a $C_1$-$C_4$ alkanol, acetone, tetrahydrofuran, dioxane or mixtures thereof, at a temperature ranging from about 0° C. to the solvent reflux temperature, for a time ranging between 1 hour and 8 hours, in particular between 2 hours and 5 hours. The hydrobromide salt of a compound of formula (III) forms first and is then converted to the free base form by suspending it for example in water, $C_1$-$C_6$ alkanols or acetone, preferably methanol or ethanol; at a temperature ranging from room temperature to the solvent reflux temperature; and adding from 1 to 1.5 equivalents, preferably from 1 to 1.1 equivalents, of an inorganic base, preferably sodium or potassium bicarbonate. Upon filtration, a compound of formula (III) separates as the free base.

In particular, a compound of formula (II), as defined above, wherein the protected amino group R is in the form of an acylamino or carbamoyl group, can be prepared by reaction of a compound of formula (IV), as defined above, with a compound of formula (V)

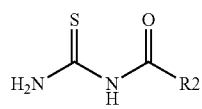

(V)

wherein $R_2$ is respectively a straight or branched $C_1$-$C_6$ alkyl or alkoxy group, optionally substituted with phenyl.

$R_2$ is preferably a $C_1$-$C_4$ alkyl group, optionally substituted with phenyl, such as methyl, ethyl, n-propyl, isopropyl, n-butyl, isobutyl, tert-butyl, benzyl or phenylethyl, in particular methyl. Alternatively, it is preferably a $C_1$-$C_4$ alkoxy group, optionally substituted with phenyl, for example methoxy, ethoxy, propoxy or benzyloxy, in particular methoxy.

The hydrobromide salt of a compound of formula (II) is first obtained, which is then converted to the free base form.

The reaction between a compound of formula (IV) and a compound of formula (V) can be carried out according to the above reported procedure by reaction between a compound of formula (IV) and thiourea. The hydrobromide salt of a compound of formula (II) can be converted to the free base form according to the procedure reported above for the transformation of a hydrobromide salt of a compound of formula (III) to the free base form.

The compounds of formula (IV) and (V) can be prepared with known methods. For example, a compound of formula (IV) can be prepared by monobromination of the corresponding ketone of formula (VI)

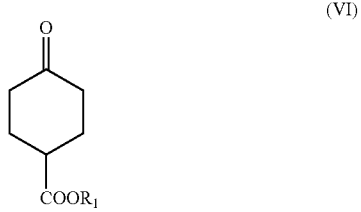

(VI)

wherein $R_1$ is as defined above, with 0.8-1.5 equivalents, preferably 1 equivalent, of bromine in a solvent selected for example from dichloromethane, toluene, acetic acid or a $C_1$-$C_4$ alkanol, in the presence of hydrobromic acid in amounts approx. ranging from 0 to 0.2 equivalents. The reaction is carried out at a temperature ranging from about −15° C. to 40° C., preferably from 0° C. to 15° C., for a time ranging between 1 hour and 6 hours, preferably between 2 hours and 5 hours. A compound of formula (VI) is commercially available.

A compound of formula (I), in particular as the single (S) enantiomer, is particularly useful in the preparation of pramipexole. Said compound is subjected to rearrangement, thereby obtaining intermediates useful in the preparation of pramipexole, according to the synthetic route disclosed in U.S. Pat. No. 4,843,086.

Therefore, a further object of the invention is the use of a compound of formula (I), typically as the single (S) enantiomer, in a process for the preparation of pramipexole or a pharmaceutically acceptable salt thereof.

In particular, in a process comprising the alkylation of a compound of formula (VII), preferably as the single (S) enantiomer,

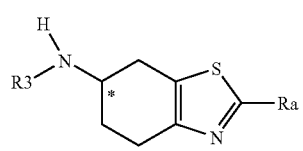

(VII)

wherein Ra is a free or protected amino group, $R_3$ is hydrogen or a $R_4$—O—CO— group, wherein $R_4$ is straight or branched $C_1$-$C_4$ alkyl and the asterisk * has the meaning defined above, to obtain a compound of formula (VIII)

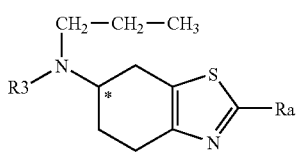

(VIII)

wherein Ra, $R_3$ and the asterisk * are as defined above, and, if necessary, the removal of the primary amino-protecting group and/or of the $R_4$—O—CO— group from the secondary amino group and, if desired, its conversion to a pharmaceutically acceptable salt thereof, characterized in that:

a) a compound of formula (VII), wherein Ra is a protected amino group and $R_3$ is as defined above, as the single (S) enantiomer, is prepared by rearrangement of a compound of formula (I), as the single (S) enantiomer, via formation of the isocyanate, and subsequent addition of a nucleophilic solvent or subsequent quenching in water in the presence of an acidic agent; or b) a compound of formula (VII), wherein Ra is a free amino group and $R_3$ is hydrogen, as the single (S) enantiomer, is prepared by rearrangement of a compound of formula (I), as the single (S) enantiomer, via formation of the isocyanate, and subsequent addition of water, to obtain a compound of formula (Ie)

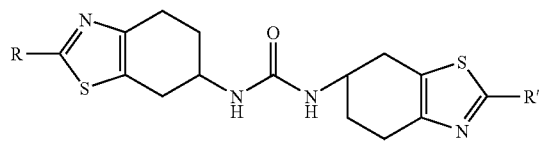

(Ie)

wherein R' has the same meaning as R, and subsequent hydrolysis.

An acidic agent is for example a mineral or an organic acid, in particular hydrochloric, sulfuric, formic or acetic acid.

A nucleophilic solvent can be for example a $C_1$-$C_4$ alkanol, typically methanol, ethanol or i-propanol.

According to process variant a) reported above, quenching in water in the presence of an acidic agent or the addition of a nucleophilic solvent respectively affords a compound of formula (VII) as defined above wherein $R_3$ is hydrogen or $R_3$ is a $R_4$—O—CO— group as defined above.

Rearrangement can be effected for example according to the Schmidt, Lossen, Hofmann or Curtius reactions.

The sequence of the products formed during the rearrangement reaction is the following:

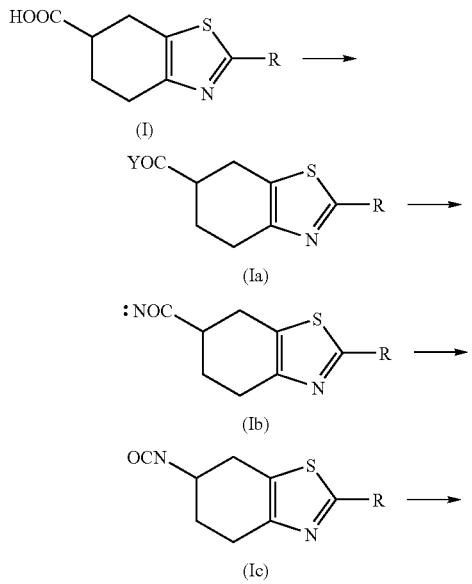

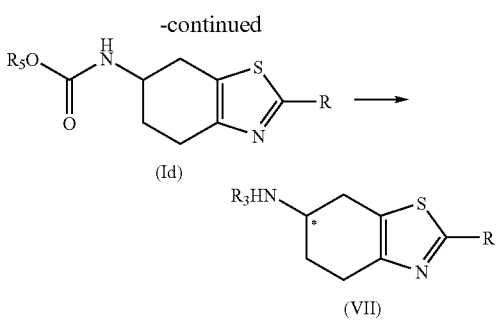

in which Y is $NHOCOR_4$, $N_3$ or $NH_2$, wherein $R_4$ is as defined above; $R_5$ is hydrogen or straight or branched $C_1$-$C_4$ alkyl; and R and $R_3$ are as defined above.

The compounds of formulae (Ia), (Ib), (Ic) and (Id) can optionally be isolated during the reaction. The compounds of formulae (Ia), (Ib), (Ic) and (Ie), either as mixture of (R,S) enantiomers or as the single (R) or (S) enantiomers, are novel compounds and are a further object of the invention.

All of the Schmidt, Lossen, Hofmann and Curtius reactions make use of an isocyanate of formula (Ic) as defined above.

A compound of formula (Ic) can be prepared according to the Schmidt reaction, treating a compound of formula (I) with hydrazoic acid in the presence of sulfuric acid, to obtain a compound of formula (Ia), wherein Y is $N_3$ and R is as defined above, which is converted to the corresponding compound of formula (Ic) by heating.

Alternatively, a compound of formula (Ic) can prepared according to the Lossen reaction, by reaction of a compound of formula (I) with a halogenating agent, preferably thionyl chloride or oxalyl chloride, and subsequent reaction with an acyl-hydroxylamine, preferably acetyl-hydroxylamine, thereby obtaining the respective acylated hydroxamic acid, i.e. a compound of formula (Ia) wherein Y is $NHOCOR_4$ and R is as defined above. Treatment of the latter with an alkali hydroxide affords a compound of formula (Ic).

Again, a compound of formula (Ic) can be prepared according to the Hofmann reaction, by transforming the carboxylic acid into amide according to known methods, i.e. into a compound of formula (Ia) wherein Y is $NH_2$ and R is as defined above, then treating it with an alkali hypohalogenite, preferably sodium hypochlorite.

Finally, a compound of formula (Ic) can be prepared according to the Curtius reaction, by reaction of a compound of formula (I) with a halogenating agent, preferably thionyl chloride or oxalyl chloride, and subsequent treatment with sodium azide to obtain the respective acyl-azide of formula (Ia) wherein Y is $N_3$ and R is as defined above; or directly with diphenylphosphorylazide, in the presence of an organic base, in particular triethylamine, diisopropylethylamine or pyridine. The acyl-azide of formula (Ia) is converted to the corresponding compound of formula (Ic) by heating.

The rearrangement reactions reported above are carried out according to known methods, for example at a temperature approx. ranging from about 10° C. to the reflux temperature, for a time ranging between 2 hours and 15 hours, preferably between 5 hours and 10 hours.

More particularly, a compound of formula (Ia), in which Y is $N_3$, is poured in water in the presence of an acidic agent, thereby converting it to a compound of formula (Id) as defined above. An acidic agent is for example a mineral or organic acid, in particular hydrochloric, sulfuric, formic or acetic acid, in amounts ranging from about 2 to about 5 mols, preferably from about 2.5 to about 3.5 mols. The reaction is carried out at a temperature ranging from room temperature to the reaction mixture reflux, preferably from about 50 to about 80° C. When the nucleophilic solvent is for example water, in the resulting compound of formula (Id) $R_5$ is hydrogen. Alternatively, when the nucleophilic solvent is for example a $C_1$-$C_4$ alkanol, in particular methanol, ethanol or i-propanol, in the resulting compound of formula (Id) $R_5$ is alkyl.

According to a preferred aspect, the rearrangement reaction to form the acyl-azide of formula (Ia) in which Y is $N_3$ is carried out according to Curtius in a nucleophilic solvent, as defined above. The reaction proceeds until formation of a compound of formula (Id) wherein $R_5$ is a straight or branched $C_1$-$C_4$ alkyl group, with no need for isolating any intermediate.

A compound of formula (Id) in which $R_5$ is hydrogen spontaneously transforms into a compound of formula (VII), wherein Ra is a protected amino group, R is as defined above and $R_3$ is hydrogen. A compound of formula (Id) in which $R_5$ is alkyl is a compound of formula (VII) wherein $R_3$ is a $R_4$—O—CO—group, as defined above and Ra is a protected amino group.

Alternatively, when a compound of formula (Ia), in which Y is $N_3$, is poured in water, or vice versa, a compound of formula (Ie)

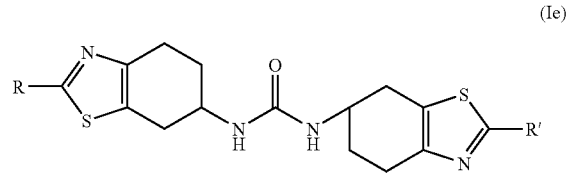

(Ie)

wherein R and R' are as defined above is obtained, which is hydrolysed to a compound of formula (VII) wherein Ra is a free amino group, $R_3$ is hydrogen and the asterisk * has the meaning defined above. The hydrolysis is typically an acidic hydrolysis, for example by treatment with hydrochloric acid according to known methods.

The alkylation of a compound of formula (VII) and, if the case, the removal of the primary amino group protecting group and, if present, of the $R_4$—O—CO— group from the secondary amino group present in a compound of formula (VIII), can be carried out according to U.S. Pat. No. 4,886,812.

It has now been found a particularly advantageous process for the conversion of a compound of formula (VII) to a compound of formula (VIII) in which $R_3$ is hydrogen and Ra is as defined above. It should be stressed that a compound of formula (VIII) in which $R_3$ is hydrogen and Ra is —$NH_2$ is pramipexole. Therefore, the invention provides a process for the preparation of pramipexole or a pharmaceutically acceptable salt thereof, comprising the acylation of a compound of formula (VII), in which $R_3$ is hydrogen and Ra is as defined above, either as a mixture of (R,S) enantiomers or as the single (S) enantiomer, by reaction with propionic anhydride and subsequent reduction of the compound of formula (IX) thus obtained,

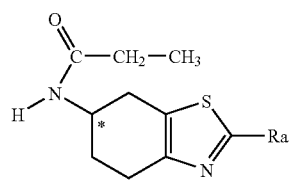

(IX)

wherein Ra is as defined above, by treatment with an alkali metal borohydride and molecular iodine to obtain a compound of formula (VIII) wherein $R_3$ is hydrogen and Ra is as defined above; followed, if necessary, by deprotection of the primary amino group and/or by resolution of the mixture of the (R,S) enantiomers into the single (S) enantiomer and, if desired, by conversion of pramipexole into a pharmaceutically acceptable salt thereof.

The acylation is preferably carried out on a compound of formula (VII), as the single (S) enantiomer, in particular having the enantiomeric purity as obtainable according to present invention. The acylation of a compound of formula (VII) with propionic anhydride can be carried out according to known methods.

An alkali metal borohydride is for example $NaBH_4$ or $KBH_4$, preferably $NaBH_4$. The amount of alkali metal borohydride used in the reduction, for example $NaBH_4$, is about 1-5 mols per mole of compound of formula (IX), preferably from about 2 to 4 mols, whereas the molar amount of iodine is about 0.5-3 mols per mole of compound of formula (IX), preferably from about 1 to 2. The reduction of a compound of formula (IX) is preferably carried out in an ether solvent, such as tetrahydrofuran, dioxane or diethyl ether, in particular tetrahydrofuran. The reaction can be carried out at a temperature ranging from about 0° C. to the reflux temperature, preferably at approx. 20-40° C.

A pramipexole pharmaceutically acceptable salt is for example an addition salt with an organic or mineral acid, as reported in U.S. Pat. No. 4,886,812, preferably the dihydrochloride, and can be obtained with known procedures.

The process of the invention for the preparation of pramipexole is particularly advantageous for the production on an industrial scale. In fact, the resolution of the enantiomers takes place during the first synthetic steps and moreover the discarded enantiomer can be recovered by racemization and recycled. This attains a reduction in the by-products of the more expensive final products and higher yields.

The following examples illustrate the invention.

EXAMPLE 1

2-Amino-4,5,6,7-tetrahydro-benzothiazole-6-carboxylic acid ethyl ester hydrobromide [(III), $R_1$=ethyl]

A 3 liter reactor equipped with mechanical stirrer, thermometer and condenser was loaded with 1500 ml of ethanol and 200 g of 4-oxo-cyclohexanecarboxylic acid ethyl ester. After cooling to 0° C., 188 g of bromine were dropped therein in about 1 hour. The temperature was raised to 10° C., then to the room one after discolouration. After 1 hour, 89.32 g of thiourea were added in portions to obtain a suspension, that was refluxed to obtain gradual dissolution of the solid. After 4 hours the solution was concentrated to small volume to obtain a solid mass, that was suspended in 800 ml of acetone and refluxed to obtain a solution. The solution was then cooled to room temperature to precipitate a solid, then to 0° C.

and after 4 hours the solid was filtered, washed twice with 100 ml of cold acetone and dried to obtain 170 g of the title product.

$^1$H-NMR in DMSO: 1.20 ppm (t, 3H); 1.79 ppm (m, 1H); 2.05 ppm (m, 1H); 2.43 ppm (t, 2H); 2.70 ppm (m, 3H); 4.08 ppm (q, 2H); 6.63 ppm (s, 2H).

EXAMPLE 2

2-Amino-4,5,6,7-tetrahydro-benzothiazole-6-carboxylic acid ethyl ester [(III), $R_1$=ethyl]

A 2 liter reactor equipped with mechanical stirrer, thermometer and condenser was loaded with 600 ml of water, 110 g of 2-amino-4,5,6,7-tetrahydro-benzothiazole-6-carboxylic acid ethyl ester hydrobromide [(III), $R_1$=ethyl] and 120 ml of methanol. The mixture was refluxed and hot filtered on a Celite bed. The resulting solution was added with a solution of 32 g of sodium bicarbonate in 300 ml of water (final pH=7-8). After 2 hours at room temperature, the precipitated white solid was filtered, washed with 100 ml of water and dried to obtain 72 g of the title product.

$^1$H-NMR in DMSO: 1.20 ppm (t, 3H); 1.79 ppm (m, 1H); 2.05 ppm (m, 1H); 2.43 ppm (t, 2H); 2.70 ppm (m, 3H); 4.08 ppm (q, 2H); 6.63 ppm (s, 2H).

EXAMPLE 3

2-Acetylamino-4,5,6,7-tetrahydro-benzothiazole-6-carboxylic acid ethyl ester [(II), $R_1$=ethyl, R=—NH—CO—CH$_3$]

A 500 ml reactor equipped with mechanical stirrer, thermometer and condenser was loaded with 280 ml of acetonitrile, 71 g of 2-amino-4,5,6,7-tetrahydro-benzothiazole-6-carboxylic acid ethyl ester [(III), $R_1$=ethyl] and 38.75 g of acetic anhydride. 38.03 g of triethylamine were dropwise added to the resulting suspension in about 10 minutes. The suspension was refluxed, obtaining complete dissolution at a temperature ranging from 70 to 75° C. After approx. 2 hours 30 minutes the solution was concentrated to dryness, and the residue was crystallized from 450 ml of isopropanol to obtain 74.5 g of 2-acetylamino-4,5,6,7-tetrahydro-benzothiazole-6-carboxylic acid ethyl ester.

$^1$H-NMR in DMSO: 1.19 ppm (t, 3H); 1.80 ppm (m, 1H); 2.09 ppm (s, 3H); 2.11 ppm (m, 1H); 2.61 ppm (t, 2H); 2.82 ppm (m, 3H), 4.08 ppm (q, 2H).

According to the same procedure, the following compounds are obtained:
 2-acetylamino-4,5,6,7-tetrahydro-benzothiazole-6-carboxylic acid methyl ester;
 2-acetylamino-4,5,6,7-tetrahydro-benzothiazole-6-carboxylic acid propyl ester;
 2-propionylamino-4,5,6,7-tetrahydro-benzothiazole-6-carboxylic acid methyl ester;
 2-propionylamino-4,5,6,7-tetrahydro-benzothiazole-6-carboxylic acid ethyl ester; and
 2-propionylamino-4,5,6,7-tetrahydro-benzothiazole-6-carboxylic acid propyl ester.

EXAMPLE 4

2-Acetylamino-4,5,6,7-tetrahydro-benzothiazole-6-carboxylic acid ethyl ester hydrobromide [(II), $R_1$=ethyl, R=—NH—CO—CH$_3$]

A 500 ml reactor equipped with mechanical stirrer, thermometer and condenser was loaded with 200 ml of methylene chloride, 20 g of 4-oxo-cyclohexanecarboxylic acid ethyl ester, 2 g of 48% hydrobromic acid. The resulting clear solution was cooled to 0° C. and dropwise added with 18.88 g of bromine in about 2 hours. Two hours after completion of the addition, 100 ml of water were added and the phases were separated, discarding the aqueous one. 80 ml of water were added and the mixture was neutralized to pH=7-8 with sodium bicarbonate. The organic phase was separated and was concentrated to one third of the original volume, then added with 150 ml of ethanol and 13.95 g of acetyl thiourea to obtain a suspension. Upon reflux, the solid gradually dissolved to obtain a clear solution. After 3 hours the solution was concentrated to small volume to obtain a solid mass, that was crystallized from 200 ml of i-propanol to obtain 15.9 g of solid.

$^1$H-NMR in DMSO: 1.2 ppm (t, 3H); 1.81 ppm (m, 1H); 2.09 ppm (m, 1H); 2.11 ppm (s, 3H); 2.60 ppm (t, 2H); 2.81 ppm (m, 3H); 4.08 ppm (q, 2H).

According to the same procedure, the following compounds are obtained, as hydrobromide:
 2-acetylamino-4,5,6,7-tetrahydro-benzothiazole-6-carboxylic acid methyl ester; and
 2-acetylamino-4,5,6,7-tetrahydro-benzothiazole-6-carboxylic acid propyl ester;
 2-propionylamino-4,5,6,7-tetrahydro-benzothiazole-6-carboxylic acid methyl ester;
 2-propionylamino-4,5,6,7-tetrahydro-benzothiazole-6-carboxylic acid ethyl ester; and
 2-propionylamino-4,5,6,7-tetrahydro-benzothiazole-6-carboxylic acid propyl ester.

EXAMPLE 5

2-Acetylamino-4,5,6,7-tetrahydro-benzothiazole-6-carboxylic acid [(I), R=—NH—CO—CH$_3$]

A 500 ml reactor equipped with mechanical stirrer, thermometer and condenser was loaded with 200 ml of water, 30 g of 2-acetylamino-4,5,6,7-tetrahydro-benzothiazole-6-carboxylic acid ethyl ester [(II), $R_1$=ethyl, R=—NH—CO—CH$_3$] and 52.2 g of 30% sodium hydroxide, keeping the temperature below 30° C.; during the addition the solid gradually solubilized until complete dissolution. After 2 hours, glacial acetic acid was dropwise added to pH=4.5-5.5; after approx. 1 hour the precipitated white solid was filtered, washed with 70 ml of water and dried to obtain 24.8 g of 2-acetylamino-4,5,6,7-tetrahydro-benzothiazole-6-carboxylic acid.

$^1$H-NMR in DMSO: 1.75 ppm (m, 1H); 2.09 ppm (s, 3H); 2.11 ppm (m, 1H); 2.58 ppm (m, 3H); 2.78 ppm (m, 2H).

$^{13}$C-NMR in DMSO: 22.48 ppm; 24.72 ppm; 25.04 ppm; 25.5 ppm; 39.37 ppm; 119.77 ppm; 143.4 ppm; 155.27 ppm; 167.99 ppm; 175.69 ppm.

According to the same procedure, 2-propionylamino-4,5,6,7-tetrahydro-benzothiazole-6-carboxylic acid is obtained.

EXAMPLE 6

N-(6-Amino-4,5,6,7-tetrahydro-benzothiazol-2-yl)-acetamide dihydrochloride, [(VII), Ra=—NH—CO—CH$_3$, $R_3$=—H]

A 500 ml reactor equipped with mechanical stirrer, thermometer and condenser was loaded with 10 g of 2-acetylamino-4,5,6,7-tetrahydro-benzothiazole-6-carboxylic acid [(I), R=—NH—CO—CH$_3$] suspended in 146 ml of N,N-dimethylformamide, and 4.63 g of triethylamine were added.

After that, a solution consisting of 12.57 g of diphenylphosphoryl azide (DPPA) dissolved in 10 ml N,N-dimethylformamide was dropped therein in 2 hours. The reaction mixture gradually solubilized during the addition until complete dissolution. After 5 hours the reaction solution was dropped in 1.3 liters of an aqueous solution containing 14 ml of 37% hydrochloric acid, at 60° C. The mixture was left to cool, then extracted twice with 200 ml of methylene chloride, discarding the organic phase. The aqueous phase was concentrated to a residue, that was crystallized from i-propanol-water to obtain 4.5 g of a white solid.

$^1$H-NMR in DMSO: 1.91 ppm (m, 1H); 2.17 ppm (s, 3H); 2.19 ppm (m, 1H); 2.73 pm (m, 3H); 3.07 ppm (dd, 1H); 3.49 ppm (s, broad, 1H); 8.39 ppm (s, broad, 2H).

$^{13}$C-NMR in DMSO: 22.50 ppm; 23.64 ppm; 26.49 ppm; 26.66 ppm; 46.56 ppm; 117.39 ppm; 142.89 ppm; 156.06 ppm; 168.28 ppm.

According to the same procedure, starting from (S)$_2$-acetylamino-4,5,6,7-tetrahydro-benzothiazole-6-carboxylic acid, (S)N-(6-amino-4,5,6,7-tetrahydro-benzothiazol-2-yl)-acetamide dihydrochloride is obtained.

EXAMPLE 7

(2-Acetylamino-4,5,6,7-tetrahydro-benzothiazol-6-yl)-carbamic acid methyl ester hydrochloride [(VII), Ra=—NH—CO—CH$_3$, R$_3$=—CO—O—CH$_3$]

A 500 ml reactor equipped with mechanical stirrer, thermometer and condenser is loaded with 5 g of 2-acetylamino-4,5,6,7-tetrahydro-benzothiazole-6-carboxylic acid [(I), R=—NH—CO—CH$_3$] suspended in 80 ml of N,N-dimethylformamide; then 2.32 g of triethylamine are added. A solution consisting of 6.3 g of diphenylphosphoryl azide (DPPA) dissolved in 7 ml N,N-dimethylformamide is dropped therein in 2 hours. The reaction mixture gradually solubilizes during the addition until complete dissolution. After 6 hours the reaction solution is dropped in 1 liter of a methanol solution containing 8 ml of 37% hydrochloric acid at 60° C. The mixture is left to cool, then extracted twice with 100 ml of methylene chloride, discarding the organic phase. The aqueous phase is concentrated to a residue that is crystallized from i-propanol-water to obtain 3.6 g of a white solid.

According to the same procedure, starting from (S)$_2$-acetylamino-4,5,6,7-tetrahydro-benzothiazole-6-carboxylic acid, (S) (2-acetylamino-4,5,6,7-tetrahydro-benzothiazol-6-yl)-carbammic acid methyl ester hydrochloride is obtained.

EXAMPLE 8

Resolution of (S)$_2$-acetylamino-4,5,6,7-tetrahydro-benzothiazole-6-carboxylic acid [(I), R=—NH—CO—CH$_3$]

A 1 liter reactor equipped with mechanical stirrer, thermometer and condenser is loaded with 50 g of 2-acetylamino-4,5,6,7-tetrahydro-benzothiazole-6-carboxylic acid [(I), R=—NH—CO—CH$_3$] suspended in 250 ml of methanol and 50 ml of water. The mixture is heated until dissolution, added with 37.3 g of (S)-(−)-α-methylbenzylamine then cooled to 25° C. The precipitated product is filtered off, washed with methanol and dried to obtain 42.8 g of a solid. This is suspended in 250 ml of methanol and 50 ml of water, heated to dissolution for 1 hour and cooled to room temperature. The suspended solid is filtered, washed with methanol and dried to obtain 32.3 g of (S)-2-acetylamino-4,5,6,7-tetrahydro-benzothiazole-6-carboxylic acid, having enantiomeric purity>99.5%.

According to the same procedure, (S)-2-propionylamino-4,5,6,7-tetrahydro-benzothiazole-6-carboxylic acid is obtained with enantiomeric purity>99.5%.

EXAMPLE 9

Resolution of (R)$_2$-acetylamino-4,5,6,7-tetrahydro-benzothiazole-6-carboxylic acid [(I), R=—NH—CO—CH$_3$]

A 1 liter reactor equipped with mechanical stirrer, thermometer and condenser are loaded with 50 g of 2-acetylamino-4,5,6,7-tetrahydro-benzothiazole-6-carboxylic acid [(I), R=—NH—CO—CH$_3$] suspended in 250 ml of methanol and 50 ml of water. The mixture is heated until dissolution, added with 37.3 g of (R)-(+)-α-methylbenzylamine, cooled to 25° C., and the precipitated product is filtered off, washed with methanol and dried to obtain 42.8 g of a solid. This is suspended in 250 ml of methanol and 50 ml of water, heated to dissolution for 1 hour and cooled to room temperature. The suspended solid is filtered, washed with methanol and dried to obtain 32.3 g of (R)-2-acetylamino-4,5,6,7-tetrahydro-benzothiazole-6-carboxylic acid, having enantiomeric purity>99.5%.

According to the same procedure, (R)-2-propionylamino-4,5,6,7-tetrahydro-benzothiazole-6-carboxylic acid is obtained with enantiomeric purity>99.5%.

EXAMPLE 10

N-{6-[3-(2-acetylamino-4,5,6,7-tetrahydro-benzothiazol-6-yl)-ureido]-4,5,6,7-tetrahydro-benzothiazol-2-yl}-acetamide, [(Ie), R=—NH—CO—CH$_3$]

A 500 ml reactor equipped with mechanical stirrer, thermometer and condenser was loaded with 10 g of 2-acetylamino-4,5,6,7-tetrahydro-benzothiazole-6-carboxylic acid [(I), R=—NH—CO—CH$_3$] suspended in 146 ml of N,N-dimethylformamide and 4.65 g of triethylamine were added. A solution consisting of 12.52 g of diphenylphosphoryl azide (DPPA) dissolved in 10 ml N,N-dimethylformamide was dropped therein in 2 hours. The reaction mixture gradually solubilized during the addition until complete dissolution. After 5 hours, the reaction mixture was dropped in 1.3 liters of an aqueous solution at 60° C. The mixture was left to cool, the separated solid was filtered, washing twice with 50 ml of water to obtain 5.9 g of a white solid.

$^1$H-NMR in DMSO: 1.72 ppm (m, 1H); 1.86 ppm (m, 1H); 2.07 ppm (s, 3H); 2.4 ppm (dd, 1H); 2.59 ppm (m, 2H); 2.8 ppm (dd, 1H); 3.93 ppm (m, 1H), 5.96 ppm (d, 1H), 11.84 ppm (s, 1H).

$^{13}$C-NMR in DMSO: 22.30 ppm; 23.74 ppm; 26.55 ppm; 26.59 ppm; 44.36 ppm; 118.42 ppm; 144.02 ppm; 156.13 ppm; 157.98 ppm, 169.18 ppm.

EXAMPLE 11

N-(6-Amino-4,5,6,7-tetrahydro-benzothiazol-2-yl)-amine dihydrochloride, [(VII), Ra=—NH$_2$, R$_3$=—H]

A 1 liter reactor equipped with mechanical stirrer, thermometer and condenser is loaded with 70 g of N-{6-[3-(2-acetylamino-4,5,6,7-tetrahydro-benzothiazol-6-yl)-ureido]-4,5,6,7-tetrahydro-benzothiazol-2-yl}-acetamide, [(Ie), R=—NH—CO—CH$_3$] suspended in 500 ml of water, and 151 g of 37% hydrochloric acid are added. The mixture is refluxed for 40 hours, then left to cool. The aqueous phase is concentrated to a residue that is crystallized from i-propanol-water to obtain 53 g of a white solid.

According to the same procedure, starting from (S)—N-{6-[3-(2-acetylamino-4,5,6,7-tetrahydro-benzothiazol-6-yl)-ureido]-4,5,6,7-tetrahydro-benzothiazol-2-yl}-acetamide, [(Ie), R=—NH—CO—CH$_3$] of enantiomeric purity 96%, (S)—N-(6-amino-4,5,6,7-tetrahydro-benzothiazol-2-yl)-amine dihydrochloride is obtained, [(VII), Ra=—NH$_2$, R$_3$=—H] with enantiomeric purity>97%.

$^1$H-NMR in DMSO: 1.91 ppm (m, 1H); 2.17 ppm (s, 3H); 2.19 ppm (m, 1H); 2.73 ppm (m, 3H); 3.07 ppm (dd, 1H); 3.49 ppm (s, broad, 1H); 8.39 ppm (s, broad, 2H).

$^{13}$C-NMR in DMSO: 22.50 ppm; 23.64 ppm; 26.49 ppm; 26.66 ppm; 46.56 ppm; 117.39 ppm; 142.89 ppm; 156.06 ppm; 168.28 ppm.

EXAMPLE 12

(S)N-(6-Propionylamino-4,5,6,7-tetrahydro-benzothiazol-2-yl)-amine; [(IX) Ra=H]

A 1 liter reactor equipped with mechanical stirrer, thermometer and condenser is loaded with under nitrogen 43.7 g of (S)N-(6-amino-4,5,6,7-tetrahydro-benzothiazol-2-yl)-amine and 220 ml of methyl ethyl ketone (MEK). Is heated a 28-32° C. and approx. 33.6 g of propionic anhydride are dropped therein in 2 hours keeping the temperature at about 28-32° C. The solution is cooled to about 0-5° C. and 109 g of 10% aqueous NaOH are added. The aqueous phase is separated; the organic phase is diluted with 60 ml of toluene and concentrated under vacuum at about 40-45° C. Under these conditions, the product starts to crystallize. The suspension is cooled to 0-5° C. and left under stirring for an hour. The precipitate is filtered with suction and washed with 10 ml of toluene.

54.2 g of (S)N-(6-propionylamino-4,5,6,7-tetrahydro-benzothiazol-2-yl)-amine are obtained.

EXAMPLE 13

Intermediate (Viii) Ra=H; Pramipexole Free Base

A 2 liter reactor under nitrogen is loaded with 53.3 g of, 33.0 g of (S) N-(6-propionylamino-4,5,6,7-tetrahydro-benzothiazol-2-yl)-amine, 95% sodium borohydride and 260 ml of tetrahydrofuran (THF). A solution of 98.7 g of iodine in 160 ml of THF is dropped therein in about 3 hours, keeping the temperature at approx. 20-25° C. The reaction mixture is kept under stirring for further 2 hours at about 20-25° C. The reaction mixture is poured into a solution of 60.0 g of 37% HCl in 260 ml of water. The mixture is heated to 50-55° C. and left under stirring for an hour. The complete cleavage of the boran-complexes is checked by HPLC. The mixture is added with 250 g of 50% aqueous NaOH, keeping the temperature at about 20-25° C. After that, 315 ml of toluene are added and the mixture is heated to about 30-35° C. Stirring is interrupted and the two phases are separated. The organic phase are washed, concentrated to a residue and dissolved in 420 ml of ethyl acetate.

The solution is concentrated under vacuum at a temperature below 50° C. to about 150 ml volume. The resulting suspension is refluxed, then cooled to about 10-15° C., stirred for further 1-2 hours, then filtered with suction and the precipitate is washed twice with 30 ml of ethyl acetate. The product is dried under vacuum at 40° C. 32 g of (S)-2-amino-6-propylamino-4,5,6,7-tetrahydrobenzothiazole are obtained.

EXAMPLE 14

Isopropyl(S)-(2-acetylamino-4,5,6,7-tetrahydro-benzothiazol-6-yl)-carbamate [(VII), Ra=—NH—CO—CH$_3$, R$_3$=—CO—O—C$_3$H$_7$]

A 2000 ml reactor equipped with mechanical stirrer, thermometer and condenser are loaded with 100 g of (S)-2-acetylamino-4,5,6,7-tetrahydro-benzothiazole-6-carboxylic acid [(I), R=—NH—CO—CH$_3$] of 97% enantiomeric purity, suspended in 700 ml of isopropanol; 84.16 g of triethylamine are added. The mixture is refluxed (about 80° C.) and a solution consisting of 120.42 g of diphenylphosphoryl azide (DPPA) is dropped therein in 2 hours. After 2 hours, the reaction mixture is cooled to 20-30° C. and added with 500 ml of water and 1.6 g of sodium hydroxide. Isopropanol is distilled off under vacuum, then 400 ml of ethyl acetate are added. The mixture is refluxed for 15 minutes, then the hot suspension is filtered through Celite. The solution is cooled to 20-30° C. and added with of 1800 ml of water. The phases are separated and the organic phase concentrated to dryness. The residue is taken up with 200 ml of acetonitrile. The suspension is heated at 50° C. for 1 hour, then cooled to 20° C. and filtered to obtain 75 g of isopropyl(S)-(2-acetylamino-4,5,6,7-tetrahydro-benzothiazol-6-yl)-carbamate, with 97% enantiomeric purity.

The invention claimed is:

1. Process for the preparation of pramipexole, or a pharmaceutically acceptable salt thereof, comprising the alkylation of a compound of formula (VII) as the single (S) enantiomer

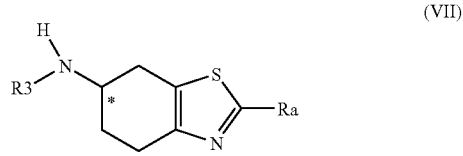

(VII)

wherein Ra is a free or protected amino group, R$_3$ is hydrogen or a R$_4$—O—CO—group, wherein R$_4$ is straight or branched C$_1$-C$_4$ alkyl and the asterisk * indicates the stereogenic carbon atom, to obtain a compound of formula (VIII)

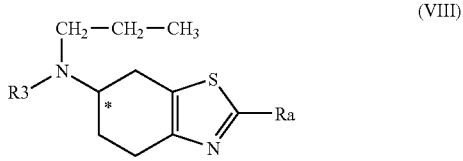

(VIII)

wherein Ra, R$_3$ and the asterisk * are as defined above, and, if necessary, the removal of the primary amino-protecting group and/or of the R$_4$—OR—CO— group from the secondary amino group and, if desired, its conversion to a pharmaceutically acceptable salt thereof, characterized in that:

a) a compound of formula (VII), wherein Ra is a protected amino group and R$_3$ is as defined above, as the single (S) enantiomer, is prepared by rearrangement of a compound of formula (I), as the single (S) enantiomer,

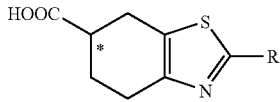
(I)

wherein R is a protected amino group; and the asterisk * indicates the stereogenic carbon atom, via formation of isocyanate, and subsequent addition of a nucleophilic solvent or subsequent quenching in water in the presence of an acidic agent; or b) a compound or formula (VII), wherein Ra is a free amino group and $R_3$ is hydrogen, as the single (S) enantiomer, is prepared by rearrangement of a compound of formula (I), as the single (S) enantiomer, via formation of isocyanate, and subsequent addition of water, to obtain a compound of formula (Ie)

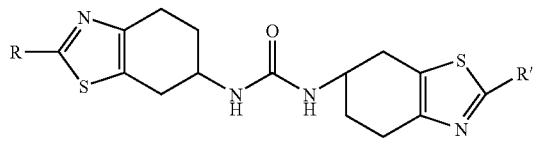
(Ie)

wherein R' has the same meaning as R defined above, and subsequent hydrolysis.

2. A process according to claim 1, variant a), wherein quenching in water in the presence of an acidic agent affords a compound of formula (VII), as defined in claim 1, wherein $R_3$ is hydrogen.

3. A process according to claim 1, variant a), wherein the nucleophilic solvent is a $C_1$-$C_4$ alkanol, to obtain a compound of formula (VII), as defined a claim 1, wherein $R_3$ is a $R_4$—O—CO— group, where $R_4$ is as defined in claim 1.

4. A process according to claim 1, variant a), wherein the rearrangement reaction is carried out according to Curtius in a nucleophilic solvent, via formation of a compound of formula (Ia)

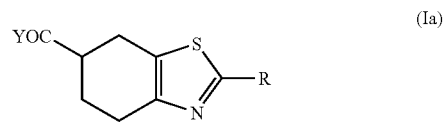
(Ia)

in which Y is $N_3$;
and of a compound of formula (Id)

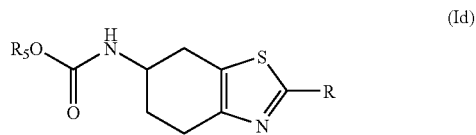
(Id)

wherein $R_5$ is a straight or branched $C_1$-$C_4$ alkyl group, without recovery of the intermediates.

5. A process according to claim 1, wherein the rearrangement takes place via formation of a isocyanate of formula (Ic)

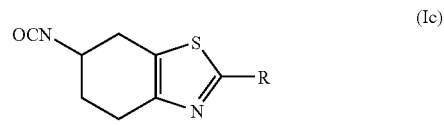
(Ic)

in which R is a protected amino group, and subsequent addition of a nucleophilic solvent or subsequent quenching in water in the presence of an acidic agent.

* * * * *